United States Patent
Medina et al.

(10) Patent No.: US 6,673,543 B2
(45) Date of Patent: Jan. 6, 2004

(54) SOLID PHASE SYNTHESIS OF LXR LIGANDS

(75) Inventors: Julio Medina, San Carlos, CA (US); Naonori Imazaki, Osaka (JP)

(73) Assignees: Tularik, Inc., So. San Francisco, CA (US); Sumitomo Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 09/827,837

(22) Filed: Apr. 4, 2001

(65) Prior Publication Data

US 2002/0072073 A1 Jun. 13, 2002

Related U.S. Application Data

(60) Provisional application No. 60/194,911, filed on Apr. 5, 2000.

(51) Int. Cl.[7] .................. C12Q 1/68; C07C 231/00; C07C 229/00
(52) U.S. Cl. ................ 435/6; 564/133; 560/38
(58) Field of Search .................. 564/133; 560/38; 435/6

(56) References Cited

U.S. PATENT DOCUMENTS

| 4,093,738 A | 6/1978 | Hubele |
| 4,166,123 A | 8/1979 | Harrison et al. |
| 4,187,232 A | 2/1980 | Evans et al. |
| 4,204,002 A | 5/1980 | Hubele |
| 4,235,928 A | 11/1980 | Eicken et al. |

FOREIGN PATENT DOCUMENTS

| WO | WO 94/21611 | 9/1994 |
| WO | WO 97/31637 | 9/1997 |
| WO | WO 99/06382 | 2/1999 |
| WO | WO 94/44987 | 9/1999 |
| WO | WO 00/54759 | 9/2000 |

OTHER PUBLICATIONS

Schwarz, M. K.; Tumelty, D.; Gallop M. A. "Solid–Phase Synthesis of 3,5–Disubstituted 2.3–Dihydro–1,5–benzothiazepin–r(5 H)– ones" J. Org. Chem. 1999, 64, 2219–2231.*

Athelstan L. J. Beckwith, etal: "Tandem Radical Translocation and Homolytic Aromatic Substitution: a Convenient and Efficient Route to Oxindoles" J. Chem. Soc. Chem. Commun.; pp. 977–978; (1995).

Sylvie Le Blanc, etal: "New Access to Spiranc β–Lactams" Tetrahedron Lett; 33(15) pp. 1993–1996 (1992).

Masazumi Ikeda, etal "Photochemistry of 2-(N–Acyl–N–alkylamino)cyclohex–2–enones: Formation of Spiro–β–lactams" Chem. Pharm. Bull; 34(12) pp. 4997–5004 (1986).

Masazumi Ikeda, etal "Photochemical Synthesis of Spiro–β–lactams" J. Chem. Soc. Chem. Commun; pp. 758–759 (1984).

* cited by examiner

Primary Examiner—Bennett Celsa
Assistant Examiner—Jon D. Epperson
(74) Attorney, Agent, or Firm—Townsend and Townsend and Crew LLP

(57) ABSTRACT

The invention provides solid support synthetic methods for producing combinatorial libraries of modulators of LXRs. The combinatorial libraries thus produced are useful both as diagnostic indicators of LXRα function and as pharmacologically active agents. The combinatorial libraries find particular use in the treatment of disease states associated with cholesterol metabolism, particularly atherosclerosis and hypercholesterolemia.

7 Claims, 3 Drawing Sheets

Scheme 2. Resins that can be employed.

SOLID PHASE SYNTHESIS OF LXR LIGANDS

CROSS-REFERENCE TO RELATED APPLICATIONS

This application claims priority to U.S. Provisional Application No. 60/194,911, filed Apr. 5, 2000, which is hereby incorporated by reference in its entirety for all purposes.

FIELD OF THE INVENTION

The present invention relates to solid phase synthetic methods, and more particularly, to solid support synthetic methods useful for producing combinatorial libraries of modulators of LXRs.

BACKGROUND OF THE INVENTION

Cholesterol is used for the synthesis of bile acids in the liver, the manufacture and repair of cell membranes, and the synthesis of steroid hormones. There are both exogenous and endogenous sources of cholesterol. The average American consumes about 450 mg of cholesterol each day and produces an additional 500 to 1,000 mg in the liver and other tissues. Another source is the 500 to 1,000 mg of biliary cholesterol that is secreted into the intestine daily; about 50 percent is reabsorbed (enterohepatic circulation). Excess accumulation of cholesterol in the arterial walls can result in atherosclerosis that is characterized by plaque formation. The plaques inhibit blood flow and promote clot formation, and can ultimately cause heart attacks, stroke and claudication. Development of therapeutic agents for the treatment of atherosclerosis and other diseases associated with cholesterol metabolism has been focused on achieving a more complete understanding of the biochemical pathways involved. Most recently, liver X receptors (LXRs) were identified as key components in cholesterol homeostasis.

The LXRs were first identified as orphan members of the nuclear receptor superfamily whose ligands and functions were unknown. Two LXR proteins α and β are known to exist in mammals. The expression of LXRα is restricted, with the highest levels being found in the liver, and lower levels found in kidney, intestine, spleen, and adrenals. See, Willy, et al., *Genes Dev.* 9(9):1033–45 (1995). LXRβ is rather ubiquitous, being found in nearly all tissues examined. Recent studies on the LXRs indicate that they are activated by certain naturally occurring, oxidized derivatives of cholesterol, including 22(R)-hydroxycholesterol, 24(S)-hydroxycholesterol, and 24,25(S)-epoxycholesterol. See, Lehmann, et al., *J. Biol. Chem.* 272(6):3137–3140 (1997). The expression pattern of LXRs and their oxysterol ligands provided the first hint that these receptors may play a role in cholesterol metabolism. See, Janowski, et al., *Nature* 383:728–731 (1996).

As noted above, cholesterol metabolism in mammals occurs via conversion into steroid hormones or bile acids. The role of LXRs in cholesterol homeostasis was first postulated to involve the pathway of bile acid synthesis, in which cholesterol 7α-hydroxylase (CYP7α) operates in a rate-limiting manner. Support for this proposal was provided when additional experiments found that the CYP7α promoter contained a functional LXR response element that could be activated by RXR/LXR heterodimers in an oxysterol- and retinoid-dependent manner.

Confirmation of LXR function as a transcriptional control point in cholesterol metabolism was made using knockout mice, particularly those lacking LXRα. See, Peet, et al., *Cell* 93:693–704 (1998). Mice lacking the receptor LXRα (e.g., knockout or (–/–) mice) lost their ability to respond normally to increases in dietary cholesterol and were unable to tolerate any cholesterol in excess of that synthesized de novo. LXRα (–/–) mice did not induce transcription of the gene encoding CYP7α when fed diets containing additional cholesterol. This resulted in an accumulation of large amounts of cholesterol in the livers of LXRα (–/–) mice, and impaired hepatic function. These results further established the role of LXRα as the essential regulatory component of cholesterol homeostasis. LXRα is also believed to be involved in fatty acid synthesis. Accordingly, the discovery of new LXRα modulators such as antagonists, via screening methods could provide treatment for a variety of lipid disorders including obesity and diabetes.

High-throughput screening techniques allow for assaying the activity of thousands of molecules in short order. However, if molecules can only be synthesized one at a time, the rate of molecule submission to the assay becomes the rate-limiting step. To remedy this situation, various combinatorial techniques have been devised and implemented. Combinatorial chemistry is defined as the repetitive and systematic covalent attachment of different structural moieties to one another to produce a mixture of numerous distinct molecular entities or target molecules (i.e., combinatorial libraries). The desired target molecules include peptides, oligonucleotides, and small organic molecules. In general, combinatorial chemistry is utilized to generate a group of structurally related analogs that can then be evaluated to establish structure-activity relationships (SAR) and to optimize biological potency.

The importance of LXRs, and particularly LXRα, to the delicate balance of cholesterol metabolism and fatty acid biosynthesis has led to the development of modulators of LXRs which are useful as therapeutic agents or diagnostic agents for the treatment of disorders associated with bile acid and cholesterol metabolism, including cholesterol gallstones, atherosclerosis, lipid storage diseases, obesity, and diabetes (see, co-pending application Ser. No. 09/479315, filed Jan. 6, 2000, incorporated herein by reference for all purposes). In view of the foregoing, there is a need in the art for combinatorial libraries of LXR modulators and the methods to produce them. The present invention fulfills this and other needs.

SUMMARY OF THE INVENTION

The importance of LXRs, and particularly LXRα to the delicate balance of cholesterol metabolism and fatty acid biosynthesis has led to the development of modulators of LXRs which are useful as therapeutic agents or diagnostic agents for the treatment of disorders associated with bile acid and cholesterol metabolism. However, more efficacious compounds are needed. As such, the present invention provides a method for preparing LXR ligands on a solid support, comprising:

(a) attaching an aniline derivative to the solid support to provide a support-bound aniline derivative;

(b) contacting the support-bound aniline derivative with an aldehyde or ketone under reductively aminating conditions to provide a support-bound substituted aniline derivative; and (c) contacting the support-bound substituted aniline derivative with an acylating agent to provide an LXR ligand on the solid support. In certain preferred embodiments, the LXR ligand or modulator is cleaved or removed from the solid support.

The methods of the present invention enable the efficient generation of modulators of LXRs and other amide-derived products following cleavage from the support. In addition, the methods of the present invention can be used to generate diverse N-substituted benzanilide derivatives which, in turn, may be used in the formation of combinatorial libraries of compounds that can subsequently be screened for biological activity.

As such, the present invention provides a combinatorial library comprising compounds having the formula:

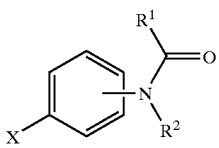

(I)

wherein $R^1$ is a group including, but not limited to, optionally substituted alkyl, optionally substituted aryl, optionally substituted ($C_8$–$C_{18}$)bicycloalkyl, optionally substituted ($C_8$–$C_{18}$)tricycloalkyl, optionally substituted ($C_8$–$C_{18}$)heterobicycloalkyl and optionally substituted ($C_8$–$C_{18}$)heterotricycloalkyl.

In a preferred embodiment, $R^1$ is a functional group including, but not limited to, optionally substituted ($C_5$–$C_{18}$)cycloalkyl or a ($C_5$–$C_{18}$)heterocycloalkyl group, more preferably a ($C_8$–$C_{18}$)bicycloalkyl, ($C_8$–$C_{18}$)tricycloalkyl, ($C_8$–$C_{18}$)heterobicycloalkyl or ($C_8$–$C_{18}$)heterotricycloalkyl group. In particularly preferred embodiments, $R^1$ represents an optionally substituted tricyclo[3.3.1.1$^{3,7}$]decanyl (or adamantyl), bicyclo[3.2.1]octanyl, bicyclo[5.2.0]nonanyl, bicyclo[4.3.2]undecanyl, tricyclo[2.2.1.0$^1$]heptanyl, tricyclo [5.3.1.1$^1$]dodecanyl, tricyclo[5.4.0.0$^{2,9}$]undecanyl, tricyclo [5.3.2.0$^{4,9}$]dodecanyl, tricyclo[4.4.1.1$^{1,5}$]dodecanyl or tricyclo[5.5.1.0$^{3,11}$]tridecanyl group. More preferably, $R^1$ is a substituted or unsubstituted adamantyl group, most preferably an unsubstituted 1-adamantyl group.

$R^2$ is a group including, but not limited to, optionally substituted alkyl, optionally substituted aryl, optionally substituted heteroaryl, optionally substituted arylalkyl and optionally substituted heteroarylalkyl. Preferred embodiments are those in which $R^2$ is aryl($C_1$–$C_8$)alkyl or heteroaryl($C_1$–$C_8$)alkyl. More preferably, $R^2$ is branched heteroaryl($C_2$–$C_8$)alkyl, for example, 1-(furan-2-yl)ethyl, 1-(pyridin-2-yl)ethyl, 1-(furan-2-yl)-2-propyl, 1-(2-pyridyl)-2-propyl, 1-(furanyl)isobutyl, 1-(3-pyridyl)isobutyl, 1-(pyridin-4-yl)ethyl, 1-(pyridin-4-yl)isobutyl, and the like. Most preferably, $R^2$ is 1-(furan-2-yl)ethyl or 1-(pyridin-2-yl)ethyl. In still other preferred embodiments, $R^2$ is a branched ($C_3$–$C_8$)alkyl, more preferably an isopropyl group. In yet other preferred embodiments, $R^2$ is a heteroaryl ($C_3$–$C_8$)alkenyl group. More preferably, $R^2$ is a 1-(3-furanyl)-3-butenyl group.

X is a functional group including, but not limited to, —$CO_2R^{11}$, —$CH_2OR^{11}$, —$C(O)R^{11}$, —$C(O)NR^{11}R^{12}$ and —$CH_2NR^{11}R^{12}$, wherein $R^{11}$ and $R^{12}$ are each members independently selected from hydrogen and optionally substituted ($C_1$–$C_8$)alkyl. In certain aspects, the present invention also provides a combinatorial library that contains substituted benzanilides, wherein the benzanilides are optionally connected to a solid support.

In yet another aspect, the present invention provides methods for synthesizing libraries of substituted benzanilides having the formula:

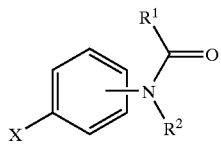

(I)

wherein
$R^1$ is a group including, but not limited to, optionally substituted ($C_5$–$C_{18}$)cycloalkyl or a ($C_5$–$C_{18}$)heterocycloalkyl group, more preferably a ($C_8$–$C_{18}$)bicycloalkyl, ($C_8$–$C_{18}$)tricycloalkyl, ($C_8$–$C_{18}$)heterobicycloalkyl or ($C_8$–$C_{18}$)heterotricycloalkyl group. In particularly preferred embodiments, $R^1$ represents an optionally substituted tricyclo[3.3.1.1$^{3,7}$] decanyl (or adamantyl), bicyclo[3.2.1]octanyl, bicyclo [5.2.0]nonanyl, bicyclo[4.3.2]undecanyl, tricyclo [2.2.1.0$^1$]heptanyl, tricyclo [5.3.1.1$^{1,5}$]dodecanyl, tricyclo[5.4.0.0$^{2,9}$]undecanyl, tricyclo[5.3.2.0$^{4,9}$] dodecanyl, tricyclo[4.4.1.1$^{1,5}$]dodecanyl or tricyclo [5.5.1.0$^{3,11}$]tridecanyl group. More preferably, $R^1$ is a substituted or unsubstituted adamantyl group, most preferably an unsubstituted 1-adamantyl group.

$R^2$ is a group including, but not limited to, optionally substituted alkyl, optionally substituted aryl, optionally substituted heteroaryl, optionally substituted arylalkyl and optionally substituted heteroarylalkyl. Preferred embodiments are those in which $R^2$ is aryl($C_1$–$C_8$)alkyl or heteroaryl($C_1$–$C_8$)alkyl. More preferably, $R^2$ is branched heteroaryl($C_2$–$C_8$)alkyl, for example, 1-(furan-2-yl)ethyl, 1-(pyridin-2-yl)ethyl, 1-(furan-2-yl)-2-propyl, 1-(2-pyridyl)-2-propyl, 1-(furanyl)isobutyl, 1-(3-pyridyl)isobutyl, 1-(pyridin-4-yl)ethyl, 1-(pyridin-4-yl)isobutyl, and the like. Most preferably, $R^2$ is 1-(furan-2-yl)ethyl or 1-(pyridin-2-yl)ethyl. In still other preferred embodiments, $R^2$ is a branched ($C_3$–$C_8$)alkyl, more preferably an isopropyl group. In yet other preferred embodiments, $R^2$ is a heteroaryl ($C_3$–$C_8$)alkenyl group. More preferably, $R^2$ is a 1-(3-furanyl)-3-butenyl group.

X is a group including, but not limited to, —$CO_2R^{11}$, —$CH_2OR^{11}$, —$C(O)R^{11}$, —$C(O)NR^{11}R^{12}$ and —$CH_2NR^{11}R^{12}$, wherein $R^{11}$ and $R^{12}$ are each members independently selected from hydrogen and optionally substituted ($C_1$–$C_8$)alkyl. In certain aspects, the present invention also provides a combinatorial library that contains substituted benzanilides, wherein the benzanilides are optionally connected to a solid support.

The present invention also provides a method for screening a library that contains a substituted benzanilide of Formula I optionally connected to a solid support.

These and other features and advantages will become more apparent when read with the accompanying drawings and detailed description that follow.

DEFINITIONS

Figure 1:
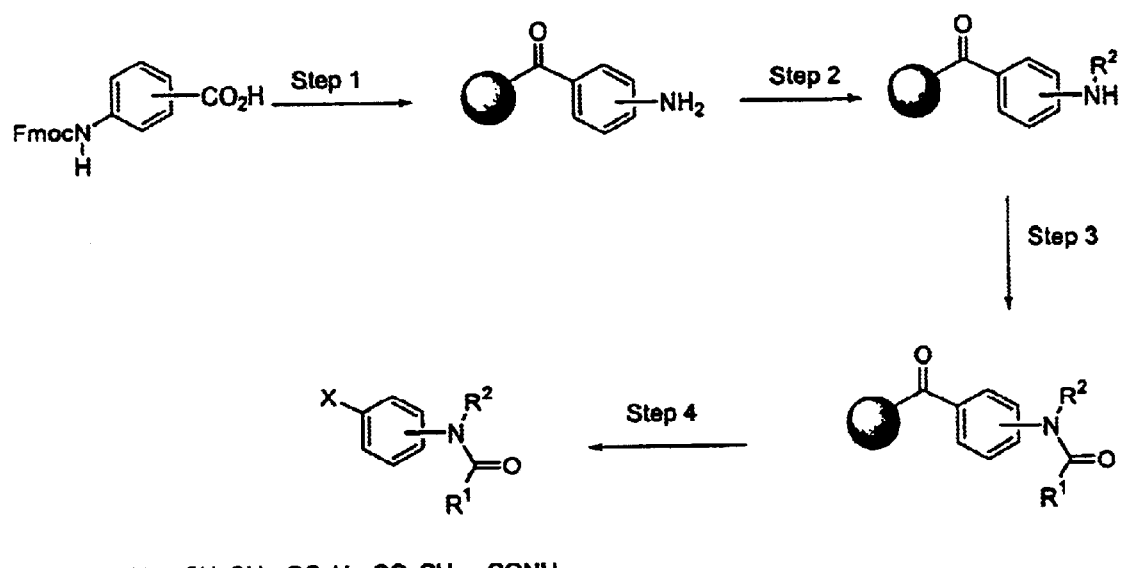
FIG. 1 illustrates general synthetic routes to substituted benzanilides using solid support technology.

As used herein, "chemical library" or "array" is an intentionally created collection of differing molecules which can be prepared synthetically and screened for biological activity in a variety of different formats (e.g., libraries of soluble molecules, libraries of molecules bound to a solid support).

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multi-radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "alkoxy," employed alone or in combination with other terms means, unless otherwise stated, an alkyl group, as defined above, connected to the remainder of the molecule via an oxygen atom, such as, for example, methoxy, ethoxy, 1-propoxy, 2-propoxy and the higher homologs and isomers.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, as well as all other linking groups described herein, no specific orientation of the linking group is implied.

The terms "cycloalkyl" and "heterocycloalkyl", by themselves or in combination with other terms, represent, unless otherwise stated, cyclic versions of "alkyl" and "heteroalkyl", respectively. The terms "cycloalkyl" and "heterocycloalkyl" are also meant to include bicyclic, tricyclic and polycyclic versions thereof. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, bicyclo[2.2.1]heptyl, bicyclo[2.2.2]octyl, adamantyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, 1,4-diazabicyclo[2.2.2]oct-2-yl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a carbon atom or a heteroatom. Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

The term "acyl" denotes the —C(O)R group, wherein R is alkyl or aryl as defined above, such as formyl, acetyl, propionyl, or butyryl.

The term "acyl halide" denotes the RC(O)X group, wherein R is alkyl or aryl as defined above, and X is a halogen.

The terms "arylalkyl" and "arylheteroalkyl" are meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 1-naphthyloxy-3-propyl, and the like). The arylalkyl and arylheteroalkyl groups will typically contain from 1 to 3 aryl moieties attached to the alkyl or heteroalkyl portion by a covalent bond or by fusing the ring to, for example, a cycloalkyl or heterocycloalkyl group. For arylheteroalkyl groups, a heteroatom can occupy the position at which the group is attached to the remainder of the molecule. For example, the term "arylheteroalkyl" is meant to include benzyloxy, 2-phenylethoxy, phenethylamine, and the like.

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R'', —SR', -halogen, —SiR'R''R''', —OC(O)R', —CO$_2$R', —CONR'R'', —OC(O)NR'R'', —NR''C(O)R', —NR''C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R'', —CN and —NO$_2$ in a number ranging from zero to (2N+1), where N is the total number of carbon atoms in such radical. R', R'' and R''' each independently refer to hydrogen, unsubstituted($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R'' are attached to the same nitrogen atom, they can be combined with the nitrogen atom to form a 5-, 6-, or 7-membered ring. For example, —NR'R'' is meant to include 1-pyrrolidinyl and 4-morpholinyl.

Similarly, substituents for the aryl groups are varied and are selected from: -halogen, —OR', —OC(O)R', —NR'R'', —SR', —R', —CN, —NO$_2$, —CO$_2$R', —CONR'R'', —OC(O)NR'R'', —NR''C(O)R', —NR''C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R'', —N$_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R' and R'' are independently selected from hydrogen, ($C_1$–$C_8$)alkyl and heteroalkyl, unsubstituted aryl, (unsubstituted aryl)-($C_1$–$C_4$)alkyl, and (unsubstituted aryl)oxy-($C_1$–$C_4$)alkyl.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$–$C_6$)alkyl.

As used herein, the term "heteroatom" is meant to include oxygen (O), nitrogen (N), sulfur (S) and silicon (Si).

DETAILED DESCRIPTION OF THE INVENTION AND PREFERRED EMBODIMENTS

A. Methods for Preparing Modulators of LXRs

The present invention provides methods for solid phase synthesis of modulators of LXRs. The methods are useful for producing combinatorial libraries of modulators of LXRs. The modulators of LXRs can be antagonists and/or agonists. As such, the present invention provides a method for preparing LXR ligands on a solid support, comprising:

(a) attaching an aniline derivative to the solid support to provide a support-bound aniline derivative;

(b) contacting the support-bound aniline derivative with an aldehyde or ketone under reductively aminating conditions to provide a support-bound substituted aniline derivative; and (c) contacting the support-bound substituted aniline derivative with an acylating agent to provide an LXR ligand on the solid support.

Various solid support materials are amenable to the methods described herein. Suitable solid supports include, but are not limited to, agarose, polyacrylamide, polystyrene, polyacrylate, hydroxyethylmethacrylate, polyamide, polyethylene, polyethyleneoxy, or copolymers and grafts of such. Other embodiments of solid-supports include small particles, non-porous surfaces, addressable arrays, etc. In certain aspects, the solid supports include, but are not limited to, polymer resins (e.g., polyethylene glycol and polystyrene), gels (e.g., polyethylene glycol gels), polyacrylamide/polyethylene glycol copolymer resins, controlled pore glass supports (e.g., the CPG supports commercially available from Millipore), and silica beads and wafers.

In certain embodiments, the solid support of the present invention has a "linker" group attached thereto that serves to append the growing modulator or "target molecule" to the solid support. Preferably, the linker is the point of cleavage following synthesis. Thus, it is advantageous that the linkers be labile to particular acid or base conditions. In certain other embodiments, the linkers are photolabile. Preferred linkers include, but are not limited to, 4-(bromomethyl)-phenoxymethyl polystyrene (e.g., Wang resin), Merrifield resin, Rink amide resin and Sieber resin. In one preferred embodiment, the solid support-bound linker is 4-[2',4'-dimethoxyphenyl)-aminomethyl]-phenoxymethyl-linked polystyrene resin ("Rink's amide resin").

FIG. 1 illustrates one particular embodiment of the present invention. FIG. 1 is merely an example that should not limit the scope of the claims herein. One of ordinary skill in the art will recognize many other variations, alternatives, and modifications. In certain embodiments, the aniline derivative to be attached to the solid support is first protected with a suitable protecting group. As used herein, "PG" or "protecting group" refers to a chemical group that exhibits the following characteristics: (1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) generated in such protected reactions. Examples of protecting groups can be found in Greene et al. (1991) *Protective Groups in Organic Synthesis*, 2nd Ed. (John Wiley & Sons, Inc., New York). A preferred protecting group is 9-fluorenylmethyloxycarbonyl or Fmoc. The Fmoc group protects the primary amine. Other protecting groups are well known to those of skill in the art.

In certain aspects, the aniline derivatives of the present invention have the formula:

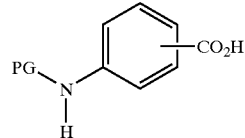

Various solvent systems can be used in the methods of the present invention. For the coupling of the aniline derivative to the linker group, an anhydrous solvent system is preferred. For example, when the Wang resin is used, coupling conditions involve for example, diisopropylethylamine (DIEA)/CsI in DMF. For use of the Rink's amide resin, the coupling conditions involve for example, benzotriazol-1-yl-oxytris(pyrrolidino)phosphonium hexafluorophosphate (PyBop)/DIEA in DMF. Those of skill in the art will know of other solvent systems and coupling reagents suitable for use in the present invention.

After the aniline derivative is coupled to the linker (step 1), the protecting group can be displaced. Various deprotection systems are well known in the art. Standard deprotection conditions include, for example, a solution comprising 20% piperidine in DMF. Those of skill in the art will know of other deprotection schemes suitable for use in the present invention.

In certain aspects, the aniline derivative that is attached to the solid support is alkylated through a reductive amination reaction with an aldehyde or a ketone using a reducing agent. The process can be stepwise (i.e., isolation of a resin-bound derivative followed by reduction) or direct (i.e., addition of carbonyl compound i.e., an aldehyde or ketone, and reduction in the same step). By contacting the support-bound aniline derivative with an aldehyde or ketone under reductively aminating conditions, the methods of the present invention provide a support-bound substituted aniline derivative (step 2). As used herein, the phrase "reductive amination conditions" refers to a reaction of an aldehyde or a ketone with a primary amine in the presence of reducing agent to yield a secondary amine. As shown in FIG. 1, the aldehyde or ketone is reductively aminated, while the primary amine is concomitantly reductively alkylated (step 2).

A variety of reducing agents are suitable for use in the methods of the present invention. Suitable reducing agents include, but are not limited to, sodium cyanoborohydride, sodium triacetoxyborohydride sodium borohydride, lithium aluminum hydride, and borane. In a preferred embodiment, sodium cyanoborohydride is used.

Various aldehydes and ketones can be used in the methods of the present invention. The aldehyde or ketone is added to the reaction mixture under reductively aminating conditions to provide a support-bound substituted aniline derivative. Suitable aldehydes include aliphatic aldehydes, aromatic aldehydes and mixtures thereof. Suitable aldehydes include, but are not limiting to, acetaldehyde, propionaldehyde, buryraldehyde, pentanal, hexanal, etc. and aromatic aldehydes including but not limited to, benzaldehyde, 1-naphthaldehyde, 4-acetoxybenzaldehyde, 4-benzoyloxybenzaldehyde, etc.

Likewise, a wide variety of ketones can be reductively aminated using the methods of the present invention. Suitable ketones include aliphatic ketones, aromatic ketones and mixtures thereof. Suitable ketones include, but are not limited to, 2-propanone, 1-(3,4-dimethoxyphenyl)-2-propanone, cyclohexanone, cyclopentanone, 3-methyl-2-butanone, 4-hydroxy-2-pentanone, 4-(4-hydroxyphenyl)-2-butanone, 2-methoxyacetone, 4,4-dimethyl-2-pentanone, diphenyl ketone, etc.

In certain instances, the ketones suitable for use in the methods of the present invention have the formula:

$$R^3\text{—}C(O)\text{—}R^4$$

wherein $R^3$ and $R^4$ are members each independently selected from optionally substituted aryl, optionally substituted heteroaryl, optionally substituted arylalkyl, optionally substituted heteroarylalkyl, and optionally substituted alkyl.

With reference to FIG. 1, after the carbonyl compound has been reductively aminated, an acylating reagent is thereafter added (step 3). Suitable acylating reagents include, but are not limited to, "acid halides" (e.g., acid chlorides like acetyl chloride and propionyl chloride, acid fluorides, and acid bromides) and "acid anhydrides" (e.g., acetic anhydride and formic acetic anhydride). The term "acid anhydride" refers to symmetrical, asymmetrical, and mixed anhydrides. The terms "acylation," "acylating," and the like, refer to a chemical reaction whereby an acyl group is added to another moiety.

In the present methods, an acyl group is added to the substituted aniline derivative to provide an LXR ligand on a solid support. Preferred acylating agents include, but are not limited to, a carboxylic acid, a carboxylate ester, a carboxylic acid halide and other activated forms of carboxylic acids, such as a reactive anhydride. Reactive acid halides include for example, acid chlorides, acid bromides, and acid fluorides. Preferred acid halides are acid chlorides.

In certain preferred methods, the acylating agents of the present invention have the formula $$R^1\text{—}Y$$

wherein: $R^1$ is selected from optionally substituted $(C_8\text{–}C_{18})$ bicycloalkyl, optionally substituted $(C_8\text{–}C_{18})$tricycloalkyl, optionally substituted $(C_8\text{–}C_{18})$heterobicycloalkyl and optionally substituted $(C_8\text{–}C_{18})$heterotricycloalkyl; and Y is selected from a carboxylic acid, a carboxylate ester, a carboxylic acid chloride and other activated forms of carboxylic acids. In a preferred embodiment, $R^1\text{—}Y$ is 1-adamantanecarbonyl chloride.

Optionally, the LXR ligand is removed from the solid support using condition well known to those of skill in the art (step 4). General mild cleavage conditions include for example, trifluoroacetic acid in water.

Figure 2:
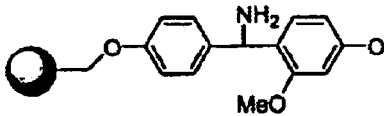
FIG. 2 illustrates various embodiments of coupling, cleavage conditions, and products formed using solid support technology of the present invention.

FIG. 2 illustrates one particular embodiment of the present invention. FIG. 2 is merely an example that should not limit the scope of the claims herein. One of ordinary skill in the art will recognize many other variations, alternatives, and modifications. In certain instances, the reagents used to cleave the molecule on the solid support will generate products having different functionalities. After the aminated product is acylated, various cleavage reagents can be used to generate an LXR modulator. Table 1 below shows various coupling/cleaving conditions and products associated with those conditions.

TABLE 1

| Resin | Coupling Conditions | Cleavage Conditions | Product |
|---|---|---|---|
| Wang or Merrifield | DIEA/CsI/DMF | TFA | —CO₂H |
|  |  | DIBAL/toluene | —CH₂OH |
|  |  | NaOMe/MeOH | —CO₂Me |
| Rink amide resin or Sieber | PyBOP/DIEA/DMF | TFA | —CONH₂ |

B. Combinatorial Synthesis

Parallel, or combinatorial synthesis has as its primary objective the generation of a library of diverse molecules which all share a common feature. By substituting different moieties at each of the variable parts of the scaffold molecule, the amount of space explorable in a library grows. Theories and modern medicinal chemistry advocate the concept of occupied space as a key factor in determining the efficacy of a given compound against a given biological target. By creating a diverse library of molecules that explores a large percentage of the targeted space, the odds of developing a highly efficacious lead compound increase dramatically.

Chemical combinatorial libraries are diverse collections of molecular compounds (see, Gordon et al. (1995) *Acc. Chem. Res.* 29:144–154). These compounds are formed using a multistep synthetic route, wherein a series of different chemical modules can be inserted at any particular step in the route. By performing the synthetic route multiple times in parallel, each possible permutation of the chemical modules can be constructed. The result is the rapid synthesis of hundreds, thousands, or even millions of different structures within a chemical class.

The various elements of the library are typically varied by, for example, the parallel dispensing of reagents to spatially addressable sites or by known "split-and-pool" combinatorial methodology. Other techniques for assembling combinatorial libraries will be apparent to those of skill in the art. See, for example, Thompson, L. A., et al., "Synthesis and Applications of Small Molecule Libraries," *Chem. Rev.* 1996, 96:555–600, and references therein which are herein incorporated by reference. See also, for example, Kaldor et al., "Synthetic Organic Chemistry on Solid Support" In, Combinatorial Chemistry and Molecular Diversity in Drug Discovery, Gordon et al., Eds., Wiley-Liss, New York, 1998.

Parallel synthesis of "small" molecules (non-oligomers with a molecular weight of 200–1000) was rarely attempted prior to 1990. See, for example, Camps. et al., *Annaks de Quimica*, 70: 848 (1990). Recently, Ellmann disclosed the solid phase-supported parallel (also referred to as "combinatorial") synthesis of eleven benzodiazepine analogs along with some prostaglandins and beta-turn mimetics. These disclosures are exemplified in U.S. Pat. No. 5,288,514. Another relevant disclosure of parallel synthesis of small molecules may be found in U.S. Pat. No. 5,324,483. This patent discloses the parallel synthesis of between 4 and 40 compounds in each of sixteen different scaffolds. Chen et al. have also applied organic synthetic strategies to develop non-peptide libraries synthesized using multi-step processes on a polymer support. (Chen et al., *J. Am. Chem. Soc.*, 116: 2661–2662 (1994)).

In one embodiment, the present invention provides a method of solid phase synthesis to generate a chemical library of single compounds that bind to the LXRα receptor using the Spatially Determined Array method. In this method, protected amines are independently attached to the solid support (see, FIG. 1, step 1) and maintained in separate flasks. After synthesis is complete, the final product is then released from the solid support through a cleavage procedure (see, FIG. 1, step 4; and Table 1). This method saves the time and effort spent in compound isolation and compound purification using the tradition solution phase methods, that often involve the isolation and purification of intermediates and final products.

In another embodiment of the present invention, a large number of solid support beads or particles are suspended in a suitable carrier (such as a solvent) in a parent container. The beads, for example, are provided with a functionalized point of attachment ("the linker") for a chemical module. The beads are then divided and placed in various separate reaction vessels. The first chemical module ("the aniline derivative") is attached to the bead, providing a variety of differently substituted solid supports. Where the first chemical module includes 3 different members, the resulting substituted beads can be represented as A1, A2, and A3.

Thereafter, the beads are washed to remove excess reagents and subsequently remixed in the parent container. The bead mixture is again divided and placed into various separate reaction vessels. The second chemical module ("the aldehyde or ketone") is coupled to the first chemical module. Where the second chemical module includes 3 different members, B1, B2, and B3, 9 differently substituted beads result: A1 B1, A1 B2, A1 B3, A2 B1, A2 B2, A2 B3, A3 B1, A3 B2, and A3 B3. Each bead will have only a single type of molecule attached to its surface.

The remixing/redivision synthetic process can be repeated until each of the different chemical modules has been incorporated into the molecule attached to the solid support. Through this method, large numbers of individual compounds can be rapidly and efficiently synthesized. For instance, where there are 3 different chemical modules, and where each chemical module contains 20 members, 8000 beads of different molecular substitution can be produced.

In general, combinatorial library synthesis can be performed either manually or through the use of an automated process. For the manual construction of a combinatorial library, a scientist would perform the various chemical manipulations. For the construction of a combinatorial library through an automated process, the various chemical manipulations will typically be performed robotically. Robotics used in conjunction with high throughput screening methods have only recently experienced general use. Development of robotics systems that can handle large numbers of resin samples for proportioning, mixing, cleavage and sample handling will continue to be developed. Moreover, robotics that can perform multiple chemical reactions at variable temperatures, and subsequently handle work up and spectroscopic characterization of bioactive leads, are or will become generally available. Manipulation of libraries containing billions of compounds will provide an impetus to improve resin loading and handling capabilities. With the availability of new assay formats, partially cleavable libraries can be advantageously employed, and solid phase assays to identify enzyme inhibitors and ligands for soluble receptors will become available. Additional selection means that enable identification of active compounds within enormous combinatorial libraries can feature affinity enrichment or affinity selection, followed by mass spectroscopic identification of any bioactive compound.

As such, the present invention provides a combinatorial library comprising compounds having the formula:

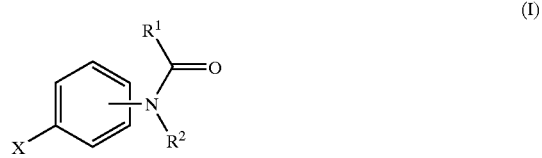

(I)

wherein

R$^1$ is a group including, but not limited to, optionally substituted (C$_5$–C$_{18}$)cycloalkyl or a (C$_5$–C$_{18}$) heterocycloalkyl group, more preferably a (C$_8$–C$_{18}$) bicycloalkyl, (C$_8$–C$_{18}$)tricycloalkyl, (C$_8$–C$_{18}$) heterobicycloalkyl or (C$_8$–C$_{18}$)heterotricycloalkyl group. In particularly preferred embodiments, R$^1$ represents an optionally substituted tricyclo[3.3.1.1$^{3,7}$] decanyl (or adamantyl), bicyclo[3.2.1]octanyl, bicyclo [5.2.0]nonanyl, bicyclo[4.3.2]undecanyl, tricyclo [2.2.1.0$^1$]heptanyl, tricyclo[5.3.1.1$^1$]dodecanyl, tricyclo[5.4.0.0$^{2,9}$]undecanyl, tricyclo[5.3.2.0$^{4,9}$] dodecanyl, tricyclo[4.4.1.1$^{1,5}$]dodecanyl or tricyclo [5.5.1.0$^{3,11}$]tridecanyl group. More preferably, R$^1$ is a substituted or unsubstituted adamantyl group, most preferably an unsubstituted 1-adamantyl group.

R$^2$ is a group including, but not limited to, optionally substituted alkyl, optionally substituted aryl, optionally substituted heteroaryl, optionally substituted arylalkyl and optionally substituted heteroarylalkyl. Preferred embodiments are those in which $R^2$ is aryl($C_1$–$C_8$)alkyl or heteroaryl($C_1$–$C_8$)alkyl. More preferably, $R^2$ is branched heteroaryl($C_2$–$C_8$)alkyl, for example, 1-(furan-2-yl)ethyl, 1-(pyridin-2-yl)ethyl, 1-(furan-2-yl)-2-propyl, 1-(2-pyridyl)-2-propyl, 1-(furanyl)isobutyl, 1-(3-pyridyl)isobutyl, 1-(pyridin-4-yl)ethyl, 1-(pyridin-4-yl)isobutyl, and the like. Most preferably, $R^2$ is 1-(furan-2-yl)ethyl or 1-(pyridin-2-yl)ethyl. In still other preferred embodiments, $R^2$ is a branched ($C_3$–$C_8$)alkyl, more preferably an isopropyl group. In yet other preferred embodiments, $R^2$ is a heteroaryl ($C_3$–$C_8$)alkenyl group. More preferably, $R^2$ is a 1-(3-furanyl)-3-butenyl group.

X is a group including, but not limited to, —$CO_2R^{11}$, —$CH_2OR^{11}$, —$C(O)R^{11}$, —$C(O)NR^{11}R^{12}$ and —$CH_2NR^{11}R^{12}$, wherein $R^{11}$ and $R^{12}$ are each members independently selected from hydrogen and optionally substituted ($C_1$–$C_8$)alkyl. In certain aspects, the present invention also provides a combinatorial library that contains substituted benzanilides, wherein the benzanilides are optionally connected to a solid support.

In another aspect, the present invention provides methods for synthesizing libraries of substituted benzanilides having the formula:

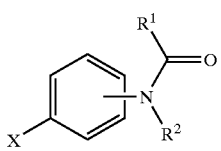

(I)

$R^1$ is a group including, but not limited to, optionally substituted ($C_5$–$C_{18}$)cycloalkyl or a ($C_5$–$C_{18}$) heterocycloalkyl group, more preferably a ($C_8$–$C_{18}$) bicycloalkyl, ($C_8$–$C_{18}$)tricycloalkyl, ($C_8$–$C_{18}$) heterobicycloalkyl or ($C_8$–$C_{18}$)heterotricycloalkyl group. In particularly preferred embodiments, $R^1$ represents an optionally substituted tricyclo[3.3.1.1$^{3,7}$] decanyl (or adamantyl), bicyclo[3.2.1]octanyl, bicyclo [5.2.0]nonanyl, bicyclo[4.3.2]undecanyl, tricyclo [2.2.1.0$^1$]heptanyl, tricyclo[5.3.1.1$^1$]dodecanyl, tricyclo[5.4.0.0$^{2,9}$]undecanyl, tricyclo[5.3.2.0$^{4,9}$] dodecanyl, tricyclo[4.4.1.1$^{1,5}$]dodecanyl or tricyclo [5.5.1.0$^{3,11}$]tridecanyl group. More preferably, $R^1$ is a substituted or unsubstituted adamantyl group, most preferably an unsubstituted 1-adamantyl group.

$R^2$ is a group including, but not limited to, optionally substituted alkyl, optionally substituted aryl, optionally substituted heteroaryl, optionally substituted arylalkyl and optionally substituted heteroarylalkyl. Preferred embodiments are those in which $R^2$ is aryl($C_1$–$C_8$)alkyl or heteroaryl($C_1$–$C_8$)alkyl. More preferably, $R^2$ is branched heteroaryl($C_2$–$C_8$)alkyl, for example, 1-(furan-2-yl)ethyl, 1-(pyridin-2-yl)ethyl, 1-(furan-2-yl)-2-propyl, 1-(2-pyridyl)-2-propyl, 1-(furanyl)isobutyl, 1-(3-pyridyl)isobutyl, 1-(pyridin-4-yl)ethyl, 1-(pyridin-4-yl)isobutyl, and the like. Most preferably, $R^2$ is 1-(furan-2-yl)ethyl or 1-(pyridin-2-yl)ethyl. In still other preferred embodiments, $R^2$ is a branched ($C_3$–$C_8$)alkyl, more preferably an isopropyl group. In yet other preferred embodiments, $R^2$ is a heteroaryl ($C_3$–$C_8$)alkenyl group. More preferably, $R^2$ is a 1-(3-furanyl)-3-butenyl group.

X is a group including, but not limited to, —$CO_2R^{11}$, —$CH_2OR^{11}$, —$C(O)R^{11}$, —$C(O)NR^{11}R^{12}$ and —$CH_2NR^{11}R^{12}$, wherein $R^{11}$ and $R^{12}$ are each members independently selected from hydrogen and optionally substituted ($C_1$–$C_8$)alkyl. In certain aspects, the present invention also provides a combinatorial library that contains substituted benzanilides, wherein the benzanilides are optionally connected to a solid support.

Figure 3:
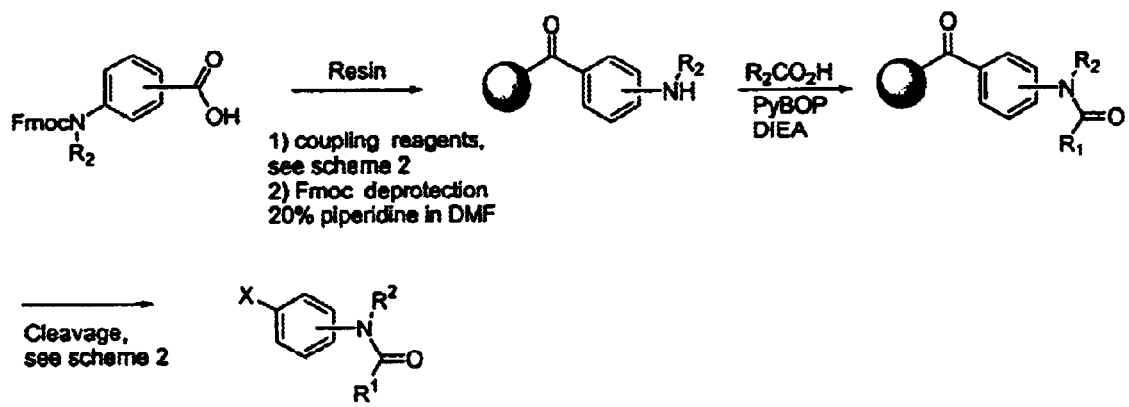
FIG. 3 illustrates a purification embodiment using solid support technology of the present invention.

The compounds of Formula I can be purified using the scheme set forth in FIG. 3, which is merely an example that should not limit the scope of the claims herein. One of ordinary skill in the art will recognize many other variations, alternatives, and modifications.

C. Screening

Screening technologies are undergoing, and will continue to undergo, considerable changes and improvements, especially with regard to functional screening techniques. One aim is development of simple and rapid functional assays that can identify one or more active ingredients in tested pools without the need for a long deconvolution process. Substantial improvements in chemistry and assay techniques will be key to achieving generalized, routine use of such assays. For instance, the scope and versatility of organic reactions conducted on solid supports are increasing. Such improvements will enrich methods and diversity relating to small molecule combinatorial libraries.

Methods for isolating library compound species that demonstrate desirable affinity for a receptor such as a LXRs or enzymes are well known in the art. For example, a receptor solution may be mixed with a solution of the compounds of a particular combinatorial library under conditions favorable to receptor-ligand binding. Specific binding of library compounds to the receptor can be detected by any of the numerous receptor bindingassays that are well known in the art. Compounds that are bound to the receptor can be readily separated from compounds that remain free in solution by applying the solution to a Sephadex G-25 gel filtration column. Free receptor and receptor-ligand complexes will pass through the column quickly, while free library compounds will be retarded in their progress through the column. The mixture of receptor-ligand complex and free receptor can then be treated with a powerful denaturing agent, such as guanidinium hydrochloride or urea, to cause release of the ligand from the receptor. The solution can then be injected onto an HPLC column (for example, a Vydac C-4 reverse-phase column, eluted with a gradient of water and acetonitrile ranging from 0% acetonitrile to 80% acetonitrile). Diode array detection can provide discrimination of the compounds of the combinatorial library from the receptor. The compound peaks can then collected and subjected to mass spectrometry for identification.

Finding a compound that inhibits an enzyme or binds to a receptor is most readily performed with free compound in solution. The compounds can also be screened while still bound to the resin used for synthesis. In some applications, this may be the preferable mode of finding compounds with the desired characteristics. For example, if a compound that binds to a specific ligand is desired, the resin-bound library of compounds can be contacted with a ligand in solution under conditions favoring a stable ligand-compound-resin complex. The bead can then be physically removed from the resin mixture and subjected to mass spectral analysis. If the synthesis has been conducted in a manner such that only one compound is likely to be synthesized on a particular bead, then the binding compound has been identified. If the synthesis has been carried out so that many compounds are present on a single bead, the information derived from analysis can be utilized to narrow the synthetic choices for the next round of synthesis and identification.

The enzyme or receptor target need not be in solution either. The receptor or enzyme may be immobilized on a column. The library of compounds may then be passed over the column, resulting in the retention of strongly binding compounds on the column after weaker-binding and non-binding compounds are washed away. The column can then be washed under conditions that dissociate protein-ligand binding, which will remove the compounds retained in the initial step. These compounds can then be analyzed, and synthesized separately in quantity for further testing. Similarly, cells bearing surface receptors can be expressed on a cell surface may be contacted with a solution of library compounds. The cells bearing bound compounds can be readily separated from the solution containing non-binding compounds. The cells can then be washed with a solution that will dissociate the bound ligand from the cell surface receptor. Again, the cells can be separated from the solution, and the solution that now contains the ligands bound in the initial step can be analyzed.

Compounds contained within the combinatorial libraries of the present invention, are capable of specifically modulating LXRs, for example regulating LXRα. Compounds may be evaluated in vitro for their ability to activate LXRα receptor function using cell-based assays such as that described in Lehmann, et al. (*J. Biol. Chem.* 1997, 272(6), 3137–3140) or biochemical assays (see co-pending application Ser. No. 08/975,614 (filed Nov. 21, 1997) and Ser. No. 09/163,713 (filed Sep. 30, 1998)). Alternatively, the libraries can be evaluated for their ability to increase or decrease gene expression modulated by LXR, using western-blot analysis. Established animal models to evaluate hypocholesterolemia effects of compounds are known in the art. For example, compounds disclosed herein can be tested for their ability to lower cholesterol levels in hamsters fed a high-cholesterol diet, using a protocol similar to that described in Spady et al. (*J. Clin. Invest.* 1988, 81, 300), Evans et al. (*J. Lipid Res.* 1994, 35, 1634), and Lin et al (*J. Med. Chem.* 1995, 38, 277). Still further, LXRα animal models (e.g., LXRα (+/−) and (−/−) mice) can be used for evaluation of the present compounds and compositions (see, for example, Peet, et al. *Cell* 1998, 93, 693–704).

The following example is provided to illustrate, but not limit, the invention.

EXAMPLE

Methods $^1$H-NMR spectra are recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electron Ionization (EI) mass spectra are recorded on a Hewlett Packard 5989A mass spectrometer. Mass spectrometry results are reported as the ratio of mass over charge, followed by the relative abundance of each ion.

Unless otherwise indicated, chemicals are obtained from Sigma Chemical Co., St. Louis, Mo. or from Aldrich Chemical Co., Inc., Milwaukee, Wis.

Combinatorial Library

1. Resins: Fourteen resin samples i.e., Fmoc-protected benzanilide derivatives are prepared and are attached to Wang resin. These resin samples are combined in a silanized beaker and mixed with DIEA/CsI and dimethyl formamide (DMF) for about 2 h. The resin sample mixture is filtered, then rinsed with DMF. The resin is then vacuum dried overnight.

2. The deprotection step proceeds with an initial washing of the resin samples with 20% piperidine in DMF for 3 min. This step removes any residual DMF from the coupling step. The actual deprotection is carried out for 20 additional min using 20% piperidine in DMF. The reaction vessels are all emptied and washed prior to the reductive amination step.

3. Reductive deamination: In a reaction vessel is placed a deprotected benzanilide derivative and benzaldehyde. To the reaction vessel is added a solution of NaCNBH$_4$.

4. Acylation reaction: The reagents contained in the vessels are thereafter acylated with benzoyl chloride.

5. Cleavage procedure: The compound mixtures are cleaved from the resin using 95% TFA (trifluoroacetic acid)/5% water into 3 ml vials. Aliquots (1.5 mL) of the cleaved solution are added to each well and mixed for 1.5 h. After emptying each reaction vessel, the resin is rinsed with another 1.0 mL of TFA cleavage solution. The TFA is removed by directing a dry nitrogen stream over the sample vials and placing the samples into a vacuum desiccator overnight.

6. Screening results: Individual samples are subjected to high throughput screening for a determination of biological LXR activity.

In order to identify agonists for LXRα, a cell-based high throughput screen was developed. Briefly, a DNA-binding domain of the nonreceptor transcription factor GAL4 was fused to the putative ligand-binding domain of LXRα. The resulting construct is introduced into 293 cells, together with an UAS-containing luciferase reporter construct. The transfected cells are then treated with the compounds and luciferase activity is measured. Compound libraries are evaluated relative to a control at a concentration of 10 μM. Luciferase activity is determined.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular reaction, material, library, process, process step or steps, to the objective, spirit and scope of the present invention. All such modifications are intended to be within the scope of the claims appended hereto. All publications, patents and patent applications mentioned in this specification are herein incorporated by reference into the specification in their entirety for all purposes.

What is claimed is:

1. A method for preparing LXR ligands on a solid support, said method comprising:

(a) attaching an aniline derivative to said solid support to provide a covalently attached support-bound aniline derivative, wherein said aniline derivative is of the formula:

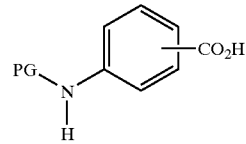

wherein PG is a protecting group;

(b) removing said protecting group;

(c) contacting said support-bound aniline derivative with an aldehyde or ketone, wherein the aldehdye is selected from the group consisting of optionally substituted (C₁–C₈)alkyl aldehyde, and an optionally substituted aryl aldehyde and a ketone selected from the group consisting of an optionally substituted dialkylketone, and a compound having the formula R³—C(O)—R⁴, wherein R³ and R⁴ are members each independently selected from the group consisting of optionally substituted aryl, optionally substituted heteroaryl, optionally substituted arylalkyl, optionally substituted heteroarylalkyl and optionally substituted alkyl, under reductively aminating conditions to provide a support-bound substituted aniline derivative; and (d) contacting said support-bound substituted aniline derivative with an acylating agent, wherein the acylating agent has the formula:

R¹—Y wherein
R¹ is a member selected from the group consisting of an optionally substituted (C₈–C₁₈)bicycloalkyl, an optionally substituted (C₈–C₁₈)tricycloalkyl, an optionally substituted (C₈–C₁₈)heterobicycloalkyl and an optionally substituted (C₈–C₁₈)heterotricycloalkyl; and Y is a member selected from the group consisting of a carboxylic acid, a carboxylate ester, a carboxylic acid chloride and other activated forms of carboxylic acids; to provide an LXR ligand on said solid support.

2. A method in accordance with claim 1, further comprising:

(e) removing said LXR ligand from said solid support.

3. A method in accordance with claim 1, wherein said solid support is selected from the group consisting of 4-(bromomethyl)phenoxymethyl polystyrene, Merrifield resin, Rink amide resin and Sieber resin.

4. A method in accordance with claim 2, wherein said LXR ligands have the formula:

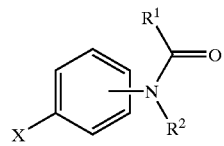

wherein
R¹ is a member selected from the group consisting of an optionally substituted (C₈–C₁₈)bicycloalkyl, an optionally substituted (C₈–C₁₈)tricycloalkyl, an optionally substituted (C₈–C₁₈)heterobicycloalkyl and an optionally substituted (C₈–C₁₈)heterotricycloalkyl;

R² is a member selected from the group consisting of an optionally substituted (C₁–C₈)alkyl, an optionally substituted aryl, an optionally substituted heteroaryl, an optionally substituted arylalkyl and an optionally substituted heteroarylalkyl; and X is a member selected from the group consisting of —CO₂R¹¹, —CH₂OR¹¹, —C(O)R¹¹, —C(O)NR¹¹R¹² and —CH₂NR¹¹R¹², wherein R¹¹ and R¹² are each members independently selected from the group consisting of hydrogen and an optionally substituted (C₁–C₈)alkyl.

5. A method in accordance with claim 4, wherein R¹ is a member selected from the group consisting of an optionally substituted optionally substituted tricyclo[3.3.1.1³,⁷]decanyl, an optionally substituted bicyclo[3.2.1]octanyl, an optionally substituted bicyclo[5.2.0]nonanyl, bicyclo[4.3.2]undecanyl an optionally substituted tricyclo[2.2.1.0¹]heptanyl, tricyclo[5.3.1.1¹]dodecanyl, an optionally substituted tricyclo[5.4.0.0²,⁹]undecanyl, an optionally substituted tricyclo[5.3.2.0⁴,⁹]dodecanyl, an optionally substituted tricyclo[4.4.1.1¹,⁵]dodecanyl and an optionally substituted tricyclo[5.5.1.0³,¹¹]tridecanyl group.

6. A method in accordance with claim 4, wherein R¹ is a substituted or an unsubstituted adamantyl group.

7. A method in accordance with claim 1, wherein said solid support is selected from the group consisting of a 4-(bromomethyl)phenoxymethyl polystyrene and Merrifield resin, and said aldehyde or ketone of step (c) is selected from the group consisting of a optionally substituted (C₁–C₅)alkyl aldehyde or ketone.

* * * * *